United States Patent [19]
Englert, Jr. et al.

[11] Patent Number: 5,237,114
[45] Date of Patent: Aug. 17, 1993

[54] REMOVAL OF CATALYST FROM CHLOROPRENE BY TREATMENT WITH OXY ACID

[75] Inventors: Joseph F. Englert, Jr., La Place; Willie Harrison, Jr., New Orleans, both of La.

[73] Assignee: E. I. Du Pont de Nemours and Company, Wilmington, Del.

[21] Appl. No.: 920,689

[22] Filed: Jul. 30, 1992

Related U.S. Application Data

[63] Continuation-in-part of Ser. No. 858,391, Mar. 20, 1992, abandoned.

[51] Int. Cl.⁵ .................. C07C 17/34; C07C 21/21
[52] U.S. Cl. .................. 570/228; 570/226; 570/230; 570/238
[58] Field of Search ............. 570/226, 228, 230, 238

[56] References Cited

U.S. PATENT DOCUMENTS

| | | | |
|---|---|---|---|
| 3,649,700 | 3/1972 | Braader | 568/238 |
| 3,754,044 | 8/1973 | Hargreaves, II et al. | 570/228 |
| 3,981,937 | 9/1976 | Campbell et al. | 570/228 |
| 4,081,461 | 3/1978 | Fox et al. | 570/397 |
| 4,418,232 | 11/1983 | Maurin, III | 570/228 |
| 4,605,800 | 11/1988 | Englert, Jr. | 570/228 |
| 4,783,559 | 11/1988 | Matsushita et al. | 568/862 |
| 5,011,968 | 4/1991 | Thunberg et al. | |

FOREIGN PATENT DOCUMENTS

| | | | |
|---|---|---|---|
| 848598 | 9/1960 | United Kingdom | 570/228 |
| 1525938 | 9/1978 | United Kingdom | 570/228 |

*Primary Examiner*—Werren B. Lone
*Attorney, Agent, or Firm*—Marilyn H. Bromels

[57] ABSTRACT

Quaternary ammonium phase transfer catalyst is removed from the dehydrochlorination product of 3,4-dichlorobutene-1 by treatment of the organic, chloroprene-containing phase with an oxy acid which combines with the catalyst to form a separate phase.

12 Claims, 2 Drawing Sheets

REMOVAL OF CATALYST FROM CHLOROPRENE BY TREATMENT WITH OXY ACID

RELATED APPLICATION

This application is a continuation-in-part of co-pending application Ser. No. 07/858,391, filed Mar. 20, 1992 now abandoned.

BACKGROUND OF THE INVENTION

This invention relates to a process for preparation of chloroprene monomer in which quaternary ammonium phase transfer catalyst is removed from the crude product by treatment with an oxy acid.

Chloroprene (2-chlorobutadiene-1,3) is an important monomer used in the manufacture of a number of synthetic elastomers. It is normally prepared by dehydrochlorination of 3,4-dichlorobutene-1 ("DCB") with aqueous alkali, for example sodium hydroxide. U.S. Pat. No. 3,981,937, Campbell et al., discloses a catalytic process for carrying out the dehydrochlorination in the presence of a quaternary ammonium salt catalyst.

In one variant of the Campbell et al. process, DCB, aqueous alkali, and the catalyst are introduced into one or more agitated reaction vessels and allowed to react at moderately elevated temperature (e.g. 50°-70° C.) until the DCB is substantially completely dehydrochlorinated. The reactor effluent contains the chloroprene product, excess aqueous alkali, brine formed in the process, the catalyst, and various organic by-products. Chloroprene is recovered from the effluent by steam-stripping.

U.S. Pat. No. 4,605,800 discloses an improvement in the process for manufacture of chloroprene. The effluent from the dehydrochlorination reactor is separated into phases, and the organic phase is steam-stripped at low temperature (below about 80° C.) to recover chloroprene product, while the steam stripper heels (containing the catalyst) are returned to the dehydrochlorination reactor. The organic phase may be treated with an acid such as, for example, acetic acid or sulfuric acid, to neutralize residual alkali prior to the steam stripping step.

Although the use of quaternary ammonium salt catalysts results in the attainment of high yields in the above-described dehydrochlorination processes, the use of these compounds is associated with certain disadvantages. For example, the presence of the catalyst causes corrosion of equipment used in recovery of chloroprene from the organic phase. In addition, the presence of catalyst in the organic phase results in entrainment of water and brine in that phase due to the surfactant properties of the catalyst.

SUMMARY OF THE INVENTION

The present invention provides a method for removal of catalyst from the dehydrochlorination product, thereby minimizing problems of entrainment and corrosion and permitting more efficient recycle of the relatively expensive catalyst. Accordingly, the invention provides a process for manufacturing chloroprene, comprising the steps of (a) dehydrochlorinating 3,4-dichlorobutene-1 by reacting said 3,4-dichlorobutene-1 with aqueous alkali in the presence of an organic quaternary ammonium compound catalyst in which the nitrogen is attached to four radicals by covalent bonds wherein at least one of the radicals is (i) a $C_6-C_{20}$ alkyl or alkenyl radical or at least two of the radicals are $C_7-C_{20}$ aralkyl radicals, or (ii) at least one of the radicals is an aralkyl radical having bonded thereto a $C_6-C_{20}$ alkyl or alkenyl radical, or (iii) at least one radical is an alkyl, alkenyl, or aralkyl radical containing up to 20 carbon atoms and containing a hydroxy or ether group in a position beta to the nitrogen, and (iv) the remaining radicals are $C_1-C_{20}$ alkyl or aralkenyl radicals, or $C_7-C_{20}$ aralkyl radicals, in one or more reactors, to provide a crude dehydrochlorination product and a chloride salt byproduct;

(b) separating the crude dehydrochlorination product into an aqueous phase and an organic phase, said organic phase containing chloroprene and quaternary ammonium compound catalyst, and said aqueous phase containing substantially all of the chloride salt byproduct;

(c) contacting the organic phase at a temperature of from about 0°-60° C. with at least 2 equivalents, per equivalent of quaternary ammonium compound catalyst, of an oxy acid selected from the group consisting of (i) inorganic acids containing at least one oxygen atom to which an acidic hydrogen is formally bound and (ii) polymeric resins having pendant inorganic oxy acid groups, the oxy acid being contained in a phase which is immiscible with said organic phase, thereby causing formation of a separate phase containing quaternary ammonium compound catalyst and oxy acid;

(d) separating the phase containing the quaternary ammonium compound catalyst and the oxy acid from the organic phase containing chloroprene; and (e) recovering chloroprene containing a substantially reduced amount of quaternary ammonium compound catalyst.

DETAILED DESCRIPTION OF THE INVENTION

Figure 1:
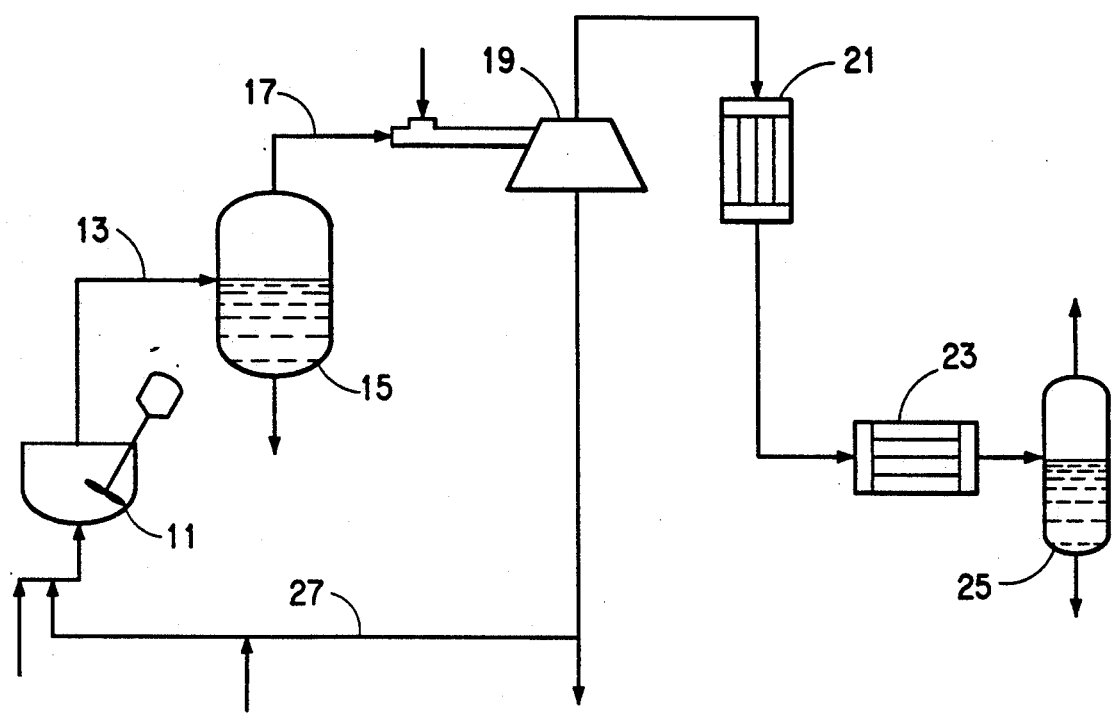
FIG. 1 is a schematic diagram of a prior art process.

Although the process of the present invention is shown in the drawings as a one-reactor process, it is not in fact so limited, and the principles of the present invention are equally applicable to a multi-reactor operation in which the reactors are arranged in series, wherein the reactants and the catalyst may all be fed either to the same reactor or to different reactors.

Referring now to FIG. 1, 11 is a reactor in which DCB is dehydrochlorinated to chloroprene by a prior art process. The reactor effluent is introduced via line 13 into decanter 15, wherein the organic phase is separated from the aqueous phase which contains brine and excess alkali. The organic phase enters through line 17 into a steam stripper 19. Crude chloroprene is removed with volatile materials, which are condensed in condenser 21, cooled in heat exchanger 23, and separated into phases in decanter 25. The crude chloroprene may be further refined, for example, by distillation (not shown). The heels from the steam-stripper 19, containing, among others, water, catalyst, high boiling organic materials, and some chloroprene, are in part recycled to reactor 11 through line 27.

Figure 2:
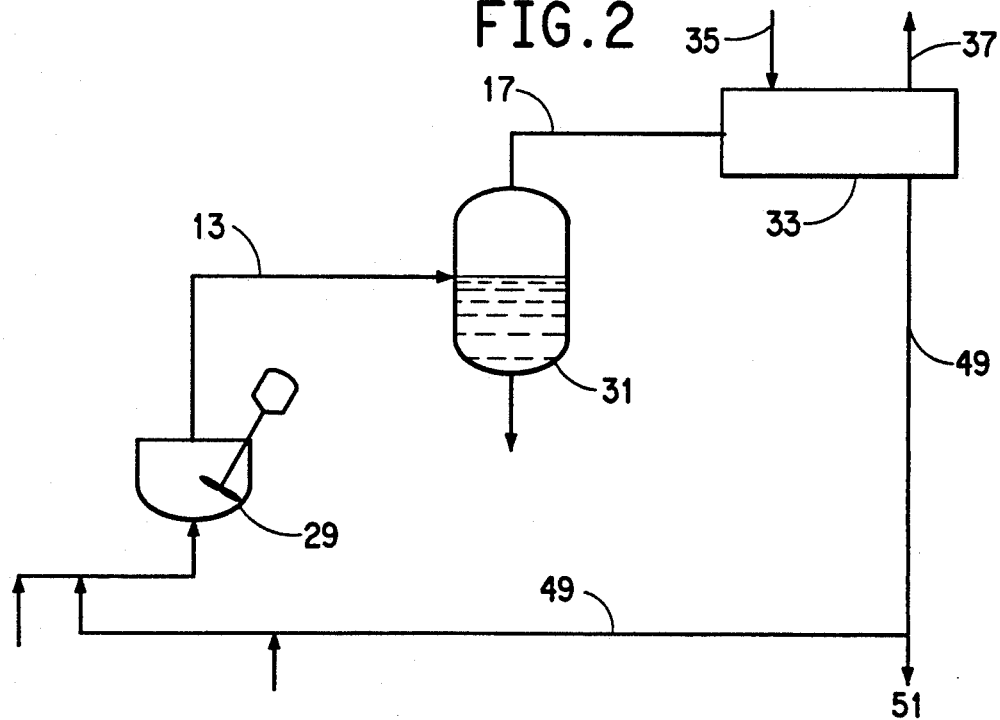
FIG. 2 is a schematic diagram of the process of the present invention.

The present invention is illustrated in FIG. 2. The reactor 29 and decanter 31 serve to contain the dehydrochlorination reaction and to separate the aqueous phase containing brine and excess alkali, as before. However, the treatment of the organic phase is quite different from that of the prior art. The organic phase, which contains the quaternary ammonium catalyst, passes to a mixing and separation device 33, where a separate phase of an oxy acid is added, 35. As a result of this addition, a separate phase forms which contains the oxy acid and at least some (and often almost all) of the quaternary ammonium catalyst. The oxy acid and catalyst phase (which may also contain water and a small amount of chloroprene) is separated and the remaining chloroprene stream 37 may be further refined if desired, for example by distillation (not shown). The present invention thus permits removal of the quaternary ammonium catalyst in a simple process without the need for steam stripping and without the need to handle corrosive catalyst materials farther downstream.

Figure 3:
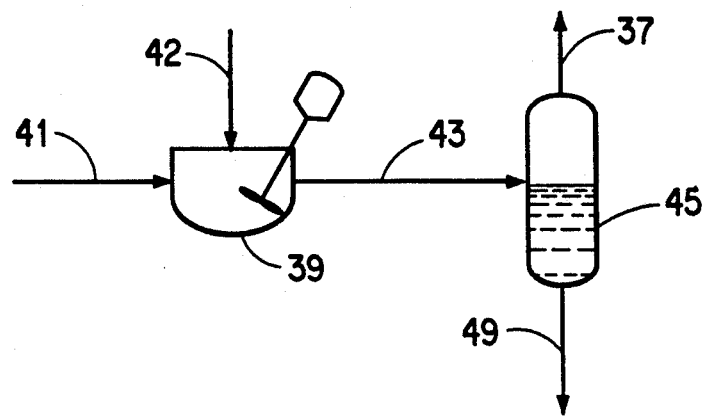
FIG. 3 is a drawing of a portion of the process showing an embodiment in which mixing and separating is effected by a stirred vessel and a decanter.

The actual formation and separation of the oxy acid and catalyst phase can be by any known methods. In one method, shown in FIG. 3, the organic phase containing the catalyst is introduced into a stirred vessel 39 via line 41. The oxy acid is added via line 42. The vessel is stirred sufficiently to permit thorough contact between the oxy acid phase and the organic phase, whereby the quaternary ammonium catalyst is transferred into the oxy acid phase. The mixture passes via line 43 to decanter 45, where the phase containing the oxy acid and the catalyst is separated.

Figure 4:
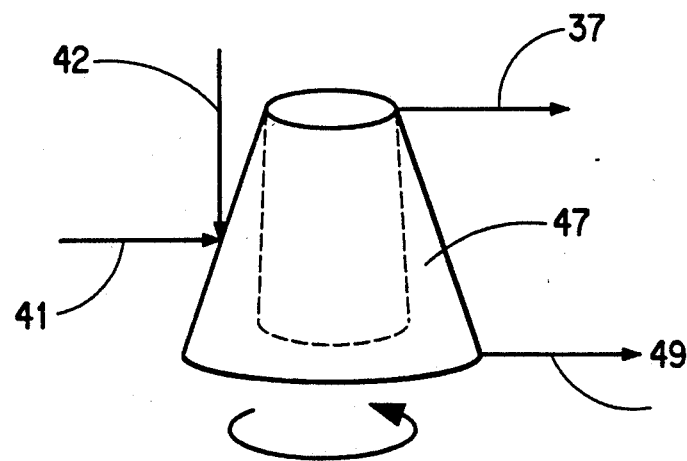
FIG. 4 is a drawing of a portion of the process showing an embodiment in which mixing and separating is effected by a centrifuge.

Alternatively, the mixing and separating may be conducted in a single piece of equipment such as a centrifuge, 47 in FIG. 4. Here the crude chloroprene in stream 41 is fed into the centrifuge along with the acid phase stream 42. The conical shaped centrifuge rotates at a high rate (e.g. 4000–8000 RPM) so that the less dense chloroprene phase 37 is directed to one exit port while the denser catalyst extract phase 49 is directed to a second exit port. The total contact and separation time is on the order of seconds to minutes. In addition, separation can be by such means as electrostatic coalescence, described in the Kirk-Othmer Encyclopedia, third edition, volume 1, pp. 673–693, or membrane separation, or other equivalent means.

The extent of mixing required in order to provide suitable contact between the organic phase and the oxy acid will depend to some extent on the level of removal of the catalyst which is desired. On a small scale it is quite adequate to stir the mixture at 350 RPM for a few minutes. Alternatively, an appropriate static mixer can be used. More generally it is adequate to subject the mixture to mixing energy of about 15 to about 109 J/sec per cubic meter (about 0.0772 to about 0.553 horsepower per thousand U.S. gallons) of organic phase for about 1 to about 15 minutes. If the mixing is not sufficiently vigorous some of the organic phase may not be adequately contacted with the oxy acid phase and extraction of the catalyst may be incomplete. Excess mixing can cause production of small, almost colloidal droplets with the result that catalyst removal is less effective and the separations are long and difficult. Thus, in some cases excess mixing can lead to less effective separation.

A wide temperature range can be used in the process of the invention. Desirably the temperature should not exceed the normal boiling point of the organic phase. Use of relatively lower temperatures also tends to minimize the corrosively of the quaternary ammonium catalyst and the oxy acid. Furthermore, formation of chloroprene dimers and polychloroprene is reduced when the lower temperatures are employed. Desirable temperature limits are about 0° C. to about 60° C., preferably about 20° to about 55° C.

The organic quaternary ammonium compounds that are used in dehydrochlorination of 3,4-dichlorobutene-1 may be chosen from many different types. The nitrogen may be substantially by four cyclic or acyclic organic groups or may be part of a ring. The quaternary compound may contain one or more than one quaternary ammonium group. The nitrogen is attached to four groups by covalent bonds. At least one of the radicals can be a $C_7$–$C_{20}$ alkyl or alkenyl radical, or at least two of the radicals can be $C_7$–$C_{20}$ aralkyl radical having bonded thereto a $C_6$–$C_{20}$ alkyl or alkenyl radical. As another alternative, at least one radical can be an alkyl, alkenyl, or aralkyl radical containing up to 20 carbon atoms and containing a hydroxy or ether group in a position beta or gamma to the nitrogen. The remaining radicals attached to the nitrogen of the organic quaternary ammonium compound can be $C_1$–$C_{20}$ alkyl or alkenyl radicals or $C_7$–$C_{20}$ aralkyl radicals. Furthermore, any two of the groups can be joined to form a ring containing the nitrogen as part of the ring. The groups on the nitrogen may be cyclic or acyclic, branched or unbranched, saturated or unsaturated. It is not essential that these radicals be free of non-hydrocarbon substituents. However, any substituents on any of the radicals must be free of functional groups capable of forming inner salts with the quaternary ammonium ion. When the quaternary nitrogen function is part of a ring, the ring must be non-aromatic; that is, the nitrogen should be connected to four aliphatic carbon atoms by single bonds. The ring may contain only carbon atoms, or other nitrogen atoms, or other members such as oxygen or sulfur atoms. Usually, the rings contain five to seven members. Fused ring systems can be used.

In general, the catalysts increase in effectiveness as the chain length of at least one substituent on the nitrogen increases. Improved effectiveness is also imparted by a hydroxy or ether group in a position beta to the nitrogen atoms.

The anion of the quaternary ammonium compound is not critical. It may be a halogen ion, a hydroxy ion, or any anion which does not interfere with the reaction and which does not promote polymerization of the chloroprene product. Most often the chloride ion is used because the chlorides are most readily available and least expensive.

The preferred catalysts for use in the present invention are (a) the compounds having the general formula $R_1R_2R_3R_4NCl$ wherein $R_1$, $R_2$, and $R_3$ are alkyl, alkenyl, or aralkyl radicals of up to about 20 carbon atoms, and $R_4$ is an alkyl or alkenyl radical of from about 6 to 20 carbon atoms or a benzyl or a $C_6$–$C_{20}$ alkyl- or alkenyl-substituted benzyl radical; and (b) compounds of the above structure in which at least one of $R_1$, $R_2$, and $R_3$ contains a hydroxy or ether group in a position beta to the nitrogen atom. Typical of the compounds of type (b) are those having the structure $$R_1R_2N[(CH_2CHO)_xH][(CH_2CHO)_yH]Cl$$
with $R_3$ and $R_4$ substituents on the indicated carbons wherein $R_1$ is a $C_6$-$C_{20}$ alkyl-substituted benzyl radical, $R_2$ is a $C_1$-$C_{20}$ alkyl or alkenyl radical or a benzyl or $C_1$-$C_{20}$ alkyl-substituted benzyl radical, $R_3$ is H or methyl, $R_4$ is H or methyl, and the sum of $x+y$ ranges from about 2 to 15.

Particularly preferred quaternary ammonium salts are the following:
($C_{12}$-$C_{18}$ alkyl)(benzyl)N(CH_2CHOHCH_3)_2Cl
($C_{12}$-$C_{18}$ alkyl)(benzyl)N(CH_2CH_2OH)_2Cl
($C_{12}$-$C_{18}$ alkyl)(benzyl)N(CH_2CH_2OH)_3Cl The amount of quaternary ammonium compound to be used in practicing the present process varies from about 0.01 to about 10% by weight, based on the weight of the 3,4-dichloro-1-butene. In the most active compounds as little as 0.01 percent may be used with advantage. In general, more than about 10% is not required and is uneconomical.

The oxy acid may be defined as any of a number of primarily inorganic acids which contain at least one oxygen atom to which an acidic hydrogen is formally bound. The term "inorganic acid" excludes carboxylic acids but includes carbonic acid and acids based on an atom other than carbon which may, however, have organic substituents. Thus, particularly suitable oxy acids include sulfuric acid and phosphoric acid. Other useful oxy acids include nitric acid, perchloric acid, chromic acid, carbonic acid, alkyl- and arylsulfonic acids such as p-toluenesulfonic acid, molybdic acid, selenic acid, sulfurous acid, tungstic acid, hypophosphorous acid, nitrous acid, and periodic acid. Also useful are polymeric materials having pendant inorganic oxy acid groups such as sulfonic acid or phosphonic acid groups. Strictly organic acids such as acetic acid are not useful for the present invention; likewise hydrochloric acid, which is not an oxy acid, is not useful.

The oxy acid should be in a phase which is substantially immiscible with the organic phase containing the quaternary ammonium compound. For most of the oxy acids described above such a phase is the concentrated aqueous phase. However, for polymeric materials having pendant inorganic oxy acid groups the polymer phase itself may be suitably immiscible with the organic phase, so that an additional aqueous component would not be required.

It is preferred to use relatively concentrated solutions of the oxy acid in the practice of the invention. Large amounts of water are generally not necessary for the extraction to proceed and would result in excessive materials handling and loss of organic material into the aqueous phase. Nevertheless, separations may be performed using an oxy acid concentration of as low as 22 weight percent or even lower. The upper concentration end will depend on the particular characteristics of the acid used; a practical upper limit would be about 98%. Carbon dioxide, as $CO_2$, is a special case included within the scope of this invention. For the purposes of this invention it is considered to be carbonic acid, although at a concentration nominally greater than 100%. This material is particularly useful in the form of supercritical $CO_2$, the handling characteristics of which are well known. Preferred concentration ranges for ordinary inorganic acids (other than supercritical $CO_2$) are about 50 to about 95%, and more preferably about 65 to about 85%. Especially preferred are concentrated sulfuric acid and concentrated phosphoric acid, the acid concentrations of which are about 65% and 85%, respectively.

The amount of the oxy acid phase which is added should be sufficient to extract the desired amount of catalyst by formation of a separate phase. This is normally about 200% or more of the theoretical amount necessary to react with the ammonium salt catalyst present. Use of an amount of acid which is merely sufficient to neutralize any minor amount of base which may be entrained in the organic phase without formation of a separate catalyst/oxy acid phase will not fulfill the objectives of the invention. Generally the amount of acid required to cause separation of a substantial amount of the catalyst from the organic phase is about ten times greater than the amount which will neutralize any nominal sodium hydroxide present in the organic phase. An amount of at least 2 equivalents acid per equivalent of catalyst will be sufficient. Generally, a range of 2-10 equivalents of acid per equivalent of catalyst is preferred and a range of 3-5 equivalents of acid per equivalent of catalyst is most preferred. Although greater amounts of acid can be used effectively, this is not economical and is not desirable unless necessary to overcome the competition of sodium ion with catalyst cations or to allow a great enough density difference for phase separation.

When relatively dilute acids are used the total amount of oxy acid phase will be relatively larger, while with more concentrated oxy acids, a smaller total amount is needed. Use of large amounts of acid can overcome the inhibitory effect of sodium ion on catalyst extraction. Also, if essentially complete removal of catalyst is desired, large amounts of acid (or repeated extractions with smaller amounts of acid) could be used. Accordingly, the total amount of oxy acid should normally be about 0.03 to about 50 percent by volume of the organic phase, preferably about 0.2 to about 5 percent, and most preferably about 0.4 to about 0.8 percent.

The concentration of catalyst in the organic phase is substantially reduced according to the process of the invention. Generally, a reduction of 90% or more is possible. At this level corrosion problems associated with the presence of catalyst in the chloroprene are essentially eliminated. However, reduction of even 30% of catalyst will result in a more efficient process.

It has been found that the presence of sodium ion inhibits the extraction of the quaternary ammonium salt by the oxy acid. Thus, for maximum efficiency, care should be taken to remove substantially all of the brine formed from the dehydrochlorination reaction before treatment with oxy acid, if sodium hydroxide is employed in the dehydrochlorination process. Alternatively, the effect of excess sodium ion can be overcome by use of higher catalyst concentrations.

The quaternary ammonium catalyst separated by treatment with oxy acid can be recycled into the dehydrochlorination reaction. In a simple scheme the catalyst-oxy acid phase is recycled directly via line 49 in FIG. 2 into reactor 29. A portion of the recycle can be purged at 51, as appropriate. Alternatively, the catalyst can be separated from the oxy acid and one or both components separately recycled. For example, a substance can be added to the catalyst-oxy acid phase which causes separation of the components. A suitable material to accomplish this separation is sodium ion, in the form of sodium hydroxide or sodium chloride. The sodium ion can be later removed by ion exchange techniques, if it is desired to recycle the acid. Alternatively the catalyst and the acid can be separated by addition of ammonium hydroxide to the catalyst-oxy acid phase. This addition causes separation of the quaternary ammonium compound from the ammonium salt and water formed from the reaction of the ammonium hydroxide with the oxy acid.

EXAMPLES 1–14

A series of extraction runs are performed using the following general method. Jacketed 500 or 1000 ml 3-neck round bottom flasks, equipped with agitators, thermometers, and nitrogen purges are charged with 350 or 500 ml, respectively, of crude chloroprene, prepared by reaction of 3,4-dichlorobutene-1 with aqueous alkali in the presence of quaternary ammonium chloride catalyst (beta-bis-hydroxypropylbenzylcocoammonium chloride). The concentration of catalyst in the crude chloroprene is 2000 to 8000 parts per million. Temperature is controlled by circulation of liquid through the jacket to heat the vessel to 25°–50° C. One to four parts by volume of the oxy acid per 1000 parts of the crude chloroprene is added and the mixture is stirred at 350 RPM for 5 minutes. The stirring is stopped and the mixture is allowed to settle for one hour. A catalyst-oxy acid adduct phase precipitates during this period. The chloroprene phase is removed and analyzed for concentration of quaternary ammonium compound. The results are shown in Table I.

TABLE I

| Ex. | Acid, conc. (%) | Amount acid (vol %) | Temp. (°C.) | Catalyst conc. (ppm) before/after extract'n | Ext'n effic. (%) | Equiv. Acid/ Equiv. Catalyst |
|---|---|---|---|---|---|---|
| 1 | H$_3$PO$_4$ 85 | 0.4 | 50 | 4500/90 | 98.0 | 3.7 |
| 2 | H$_3$PO$_4$ 85 | 0.4 | 50 | 4889/44 | 99.1 | 3.4 |
| 3 | H$_3$PO$_4$ 85 | 0.4 | 50 | 3868/116 | 97.0 | 4.4 |
| 4 | H$_3$PO$_4$ 85 | 0.4 | 50 | 5038/67 | 98.7 | 3.3 |
| 5 | H$_3$PO$_4$ 85 | 0.2 | 50 | 2000/69 | 96.6 | 4.2 |
| 6 | H$_3$PO$_4$ 85 | 0.2 | 50 | 2080/47 | 97.7 | 4.0 |
| 7 | H$_3$PO$_4$ 85 | 0.1 | 50 | 2000/78 | 96.1 | 8.4 |
| 8 | H$_3$PO$_4$ 85 | 0.1 | 50 | 2000/67 | 97.0 | 8.4 |
| 9 | H$_3$PO$_4$ 85 | 0.1 | 50 | 2000/151 | 92.4 | 8.4 |
| 10 | H$_2$SO$_4$ 84 | 0.6 | 25 | 1884/67 | 96.4 | 59.6 |
| 11 | H$_2$SO$_4$ 84 | 0.4 | 50 | 7400/238 | 96.8 | 10.1 |
| 12 | H$_2$SO$_4$ 65 | 1.6 | 50 | 3168/159 | 95.0 | 84.8 |
| 13 | H$_2$SO$_4$ 65 | 0.8 | 50 | 2200/66 | 97.0 | 61.1 |
| 14 | H$_2$SO$_4$ 65 | 0.4 | 50 | 2200/110 | 95.0 | 30.5 |

The results show that chloroprene having a substantially reduced concentration of ammonium compound catalyst is obtained by treatment with oxy acid. Both phosphoric acid and sulfuric acid are effective at removal of catalyst at concentrations as low as 0.1 weight percent and at least as high as 1.6 weight percent.

EXAMPLE 15

An extraction run is performed as in Example 1, except that the extracting acid used is 75% aqueous toluenesulfonic acid. The amount of acid solution is 3 ml for 1 liter of crude chloroprene containing 3300 ppm catalyst, which corresponds to 16.9 equivalents of acid per equivalent of ammonium salt catalyst. After agitation for one hour the mixture is allowed to stand and the phases separate, albeit slowly. The amount of catalyst remaining in the chloroprene is 628 ppm after one hour.

EXAMPLE 16

The efficiency of catalyst removal by an ion exchange resin is examined by treating crude chloroprene, prepared by dehydrochlorination of 3,4-dichlorobutene-1 with aqueous alkali in the presence of beta-bis-hydroxypropylbenzylcocoammonium chloride, and containing 3369 ppm of catalyst (free of sodium ion) with varying amounts of ion exchange resin. To each of five flasks is added 300 ml of the crude chloroprene and XN-1010 TM sulfonic acid macroreticular resin, available from Rohm and Haas, in an amount indicated in Table II. After equilibration for 20 hours at 24° C., the amount of catalyst remaining in the organic solution phase is measured. The results, shown in Table II, indicate that the ion exchange resin is effective at removal of the phase transfer catalyst:

TABLE II

| Flask | Am't of resin, g | Remaining catalyst, ppm |
|---|---|---|
| 0 | 0 | 3369 |
| 1 | 2.43 | 2778 |
| 2 | 3.72 | 2266 |
| 3 | 7.63 | 1305 |
| 4 | 18.9 | 825 |

Similar results are observed at 0° C. to −10° C. The amounts of acid range from 2.4–18.7 equivalents of acid per equivalent of ion exchange resin catalyst.

EXAMPLES 17–23

A variety of ion exchange resins are tested by placing 100 ml of resin in a 15 cm (6 inch) column. After methanol pretreatment of the column, a total of 500 ml crude chloroprene is passed therethrough at a rate of 8 ml/minute. The crude chloroprene contains about 2290 ppm of catalyst. The amount of residual catalyst in the effluent is shown in Table III.

TABLE III

| Ex. | Resin | Residual catalyst (ppm) |
|---|---|---|
| 17 | Duolite TM S37 phosphonic acid polystyrene matrix resin | 325 |
| 18 | Amberlite TM 200 sulfonic acid resin | <10 |
| 19 | Amberlite TM 252 sulfonic acid resin | 403 |
| 20 | Duolite TM S37 phosphonic acid resin | 325 |
| 21 | Sulfonated coal, washed with 6N HCl, then water and methanol | 880* |
| 22 | Duolite TM S76 phosphonic acid resin | <12 |

TABLE III-continued

| Ex. | Resin | Residual catalyst (ppm) |
|---|---|---|
| 23 | Duolite ™ S761 phosphonic acid resin | >500* |

*initial concentration 2889 ppm.

the amount of acid used is about 17 equivalents for 100 ml bed of 1.0 meq/ml resin.

EXAMPLE 24

Example 13 is repeated except that the amount of acid used is about 2.5 volume %, the excess being used to compensate for the presence of 1000 ppm NaCl. Separation within a 100 ml sample of the product is effected by spinning for 5 minutes in a centrifuge at 4000 RPM. This treatment reduces the amount of catalyst in the chloroprene from 2200 ppm to 117 ppm, an efficiency of 95%.

EXAMPLE 25

A jacketed 500 ml 3-neck round bottom flask, equipped with agitator, thermometer, and nitrogen purge is charged with 350 ml of crude chloroprene, prepared by reacting 3,4-dichlorobutene-1 with aqueous alkali in the presence of beta-bis-hydroxypropylbenzylcocoammonium chloride. The concentration of catalyst in the crude chloroprene is 3000 parts per million. Temperature is controlled by circulation of liquid through the jacket to heat the vessel to 25°-50° C. 0.14 ml of 70% nitric acid, which corresponds to 15.3 equivalents of acid per equivalent of ammonium salt catalyst, is added to the flask and the mixture is stirred for 15 minutes at 25° C. Stirring is stopped and the mixture is allowed to settle for one hour. A catalyst-oxy acid adduct phase precipitates during this period and is separated from the chloroprene-containing organic phase. The catalyst removal efficiency is greater than 90%.

We claim:

1. A process for manufacturing chloroprene comprising the steps of:
   (a) dehydrochlorinating 3,4-dichlorobutene-1 by reacting said 3,4-dichlorobutene-1 with aqueous alkali in the presence of an organic quaternary ammonium compound catalyst containing one or more quaternary ammonium groups wherein the quaternary ammonium cations are represented by the following structure $R_1R_2R_3R_4N$ where $R_1$, $R_2$, and $R_3$ are selected from the group consisting of a) cyclic or acyclic $C_7$-$C_{20}$ alkyl radicals, $C_7$-$C_{20}$ alkenyl radicals, $C_7$-$C_{20}$ aralkyl radicals, and $C_7$-$C_{20}$ aralkyl radicals having bonded thereto a $C_6$-$C_{20}$ alkyl or alkenyl radical, and b) acyclic alkyl, alkenyl, or aralkyl radicals of up to 20 carbon atoms wherein a hydroxy or ether group is in a position beta or gamma to the nitrogen atom, and $R_4$ is selected from the group consisting of $C_1$-$C_{20}$ alkyl or aralkenyl radicals, and $C_7$-$C_{20}$ aralkyl radicals, in one or more reactors, to provide a crude dehydrochlorination product and a chloride salt by product;
   (b) separating the crude dehydrochlorination product into an aqueous phase and an organic phase, said organic phase containing chloroprene and quaternary ammonium compound catalyst, and said aqueous phase containing substantially all of the chloride salt byproduct;
   (c) contacting the organic phase at a temperature of from about 0°-60° C. with at least 2 equivalents, per equivalent of quaternary ammonium compound catalyst, of an oxy acid selected from the group consisting of (i) inorganic acids containing at least one oxygen atom to which an acidic hydrogen is formally bound and (ii) polymeric resins having pendant inorganic oxy acid groups, the oxy acid being contained in a phase which is immiscible with said organic phase, thereby causing formation of a separate phase containing quaternary ammonium compound catalyst and oxy acid;
   (d) separating the phase containing the quaternary ammonium compound catalyst and the oxy acid from the organic phase containing chloroprene; and
   (e) recovering chloroprene containing a substantially reduced amount of quaternary ammonium compound catalyst.

2. The process of claim 1 wherein the oxy acid is aqueous and is selected from the group consisting of phosphoric acid, sulfuric acid, nitric acid, perchloric acid, chromic acid, carbonic acid, alkyl- and arylsulfonic acids, molybdic acid, selenic acid, sulfurous acid, tungstic acid, hypophosphorous acid, nitrous acid, and periodic acid.

3. The process of claim 1 wherein the oxy acid is a polymeric resin containing pendant sulfonic or phosphonic acid groups.

4. The process of claim 1 wherein the oxy acid is selected from the group consisting of aqueous sulfuric acid and aqueous phosphoric acid.

5. The process of claim 4 wherein the concentration of the acid is about 22 to about 98 weight percent.

6. The process of claim 1 wherein the amount of oxy acid added is 1-10 equivalents per equivalent of quaternary ammonium compound catalyst.

7. The process of claim 4 wherein the volume of oxy acid added is about 0.03 to about 50 percent of the volume of the organic phase.

8. The process of claim 1 further comprising the step of:
   (f) recycling at least some of the quaternary ammonium compound catalyst recovered from the separation step into the dehydrochlorination step.

9. The process of claim 8 wherein at least some of the recovered quaternary ammonium compound catalyst is introduced into the dehydrochlorination step without separation from the oxy acid.

10. The process of claim 8 wherein the quaternary ammonium compound catalyst is separated from the oxy acid before it is introduced into the dehydrochlorination step.

11. The process of claim 1 wherein the quaternary ammonium compound catalyst is a quaternary ammonium chloride or a quaternary ammonium hydroxide.

12. The process of claim 1 wherein the quaternary ammonium compound catalyst is represented by the following structure $$R_1R_2N[(CH_2CHO)_xH]\overset{R_3}{|}[(CH_2CHO)_yH]\overset{R_4}{|}Cl$$

where
$R_1$ is a $C_6$-$C_{20}$ alkyl-substituted benzyl radical,
$R_2$ is a $C_1$-$C_{20}$ alkyl or alkenyl radical, or a benzyl or $C_1$-$C_{20}$ alkyl-substituted benzyl radical,
$R_3$ is H or methyl,
$R_4$ is H or methyl,
and the sum of x+y ranges from about 2 to 15.

* * * * *

UNITED STATES PATENT AND TRADEMARK OFFICE
CERTIFICATE OF CORRECTION

PATENT NO.   :   5,237,114
DATED        :   Aug. 17, 1993
INVENTOR(S)  :   Joseph F. Englert, Jr. and Willie Harrison, Jr.

It is certified that error appears in the above-identified patent and that said Letters Patent is hereby corrected as shown below:

Column 10, Claim 6, line 34, change "1-10" to -- 2-10 --.

Signed and Sealed this

Fifth Day of April, 1994

Attest:

BRUCE LEHMAN

Attesting Officer

Commissioner of Patents and Trademarks